United States Patent
Bauerfeind et al.

(10) Patent No.: US 10,524,951 B2
(45) Date of Patent: Jan. 7, 2020

(54) EPICONDYLITIS PAD

(71) Applicant: BAUERFEIND AG, Zeulenroda-Triebes (DE)

(72) Inventors: Hans B. Bauerfeind, Zeulenroda-Triebes (DE); Rainer Scheuermann, Schwentinental (DE); Joachim Böckelmann, Kempen (DE)

(73) Assignee: BAUERFEIND AG (DE)

( * ) Notice: Subject to any disclaimer, the term of this patent is extended or adjusted under 35 U.S.C. 154(b) by 0 days.

(21) Appl. No.: 16/069,276

(22) PCT Filed: Jan. 13, 2017

(86) PCT No.: PCT/EP2017/050654
§ 371 (c)(1),
(2) Date: Jul. 11, 2018

(87) PCT Pub. No.: WO2017/121844
PCT Pub. Date: Jul. 20, 2017

(65) Prior Publication Data
US 2019/0021896 A1 Jan. 24, 2019

(30) Foreign Application Priority Data

Jan. 13, 2016 (DE) .................. 10 2016 000 490

(51) Int. Cl.
*A61F 5/30* (2006.01)
*A61F 5/01* (2006.01)
(Continued)

(52) U.S. Cl.
CPC .............. *A61F 5/30* (2013.01); *A61F 5/0118* (2013.01); *A61F 5/24* (2013.01); *A61F 5/28* (2013.01)

(58) Field of Classification Search
CPC .................................................... A61F 13/101
(Continued)

(56) References Cited

U.S. PATENT DOCUMENTS

| 18,708 A | * | 11/1857 | Riggs | ........................ A61F 5/24 |
| | | | | 128/115.1 |
| 5,048,542 A | * | 9/1991 | Murray | ................. A61F 15/004 |
| | | | | 128/846 |

(Continued)

FOREIGN PATENT DOCUMENTS

| DE | 295 09 871 U1 | 5/1995 |
| DE | 197 16 705 C1 | 5/1998 |

(Continued)

OTHER PUBLICATIONS

Feb. 19, 2019 First Office Action from National Intellectual Property Administration of the P.R.C. in related pending case.

(Continued)

*Primary Examiner* — Keri J Nelson
(74) *Attorney, Agent, or Firm* — Durham Jones & Pinegar; Sarah W. Matthews

(57) ABSTRACT

Described herein is a truss pad having a base body, wherein the base body comprises a first surface and a second surface opposite the first surface, wherein the first surface of the base body comprises five pressure pads, wherein the first pressure pad is located in the center of a rectangle that is formed by the second pressure pad, the third pressure pad, the fourth pressure pad, and the fifth pressure pad.

16 Claims, 3 Drawing Sheets

(51) Int. Cl.
*A61F 5/24* (2006.01)
*A61F 5/28* (2006.01)

(58) Field of Classification Search
USPC ..... 128/95.1, 99.1, 106.1, 107.1, 112.1, 878, 128/881
See application file for complete search history.

(56) References Cited

U.S. PATENT DOCUMENTS

| | | | |
|---|---|---|---|
| 6,007,508 | A | 12/1999 | Reinhardt et al. |
| 6,398,749 | B1 | 6/2002 | Slautterback |
| 2003/0032912 | A1* | 2/2003 | Weaver, II ............ A61F 13/108 602/62 |
| 2008/0262536 | A1 | 10/2008 | Babaev |
| 2010/0113996 | A1 | 6/2010 | Batz et al. |

FOREIGN PATENT DOCUMENTS

| | | |
|---|---|---|
| DE | 697 23 229 T2 | 12/2004 |
| DE | 602 24 057 T2 | 11/2008 |
| DE | 10 2008 055867 A1 | 6/2010 |
| DE | 202014005972 U1 | 8/2014 |
| EP | 0485943 A1 | 5/1992 |
| KR | 200437182 Y | 11/2007 |

OTHER PUBLICATIONS

International Preliminary Report on Patentability from related PCT/EP2017/050654 dated Dec. 13, 2017.
International Search Report, dated Apr. 4, 2017 from related PCT/EP2017/050654.

* cited by examiner

EPICONDYLITIS PAD

CROSS-REFERENCE TO RELATED APPLICATIONS

This application is a 371 of international application PCT/EP2017/050654, filed 2017 Jan. 13, which claims priority to DE 102016000490, filed 2016 Jan. 13, each of which is incorporated herein by reference.

FIELD OF INVENTION

The invention relates to a truss pad for an epicondylitis brace, epicondylitis bandage, or epicondylitis orthosis and to an epicondylitis brace, epicondylitis bandage, or epicondylitis orthosis comprising a truss pad according to the invention.

BACKGROUND

Epicondylitis is an acquired painful inflammation of the tendon entheses of muscles of the forearm that originate at the two bone protuberances superior to the epicondyle at the distal part of the humerus. Epicondylitis develops by overstraining the forearm muscles. Two types of epicondylitis are known, namely firstly epicondylitis radialis humeri, also known as tennis elbow or tennis arm, at the lateral epicondyle of the humerus, i.e. the extensor muscle of the wrist and fingers, and secondly epicondylitis ulnaris humeri, also known as golf elbow or golf arm, at the medial epicondyle of the humerus, i.e. the flexor muscle of the wrist and fingers.

Tennis elbow and golf elbow are treated using appropriate bandages and braces, among other things, as known, for example, in their basic shape from the utility models DE 83 123 60 U1 and DE 94 171 91 U1. DE 197 16 705 C1 and DE 10 2008 055 867 A1 describe epicondylitis braces in which specifically-shaped truss pads are adapted to use either on the right or on the left arm by turning or changing the positions of the truss pads. With these truss pads, it is only possible to ensure indication-appropriate care of the patient by repositioning, in particular turning, the truss pad. However, this is often times not done correctly or not done at all. While treatment of golf elbow is not at all provided for in DE 197 16 705 C1, treatment of golf elbow with a brace from DE 10 2008 055 867 A1 is only possible by means of different attachment options of the truss pad on the brace.

SUMMARY

Disclosed herein is a truss pad having a base body, wherein the base body may comprise a first surface and a second surface opposite the first surface, wherein the first surface of the base body may comprise pressure pads, characterized in that the first surface of the base body may comprise exactly five pressure pads, wherein the first pressure pad may be located in the center of a rectangle that is formed by the second pressure pad, the third pressure pad, the fourth pressure pad, and the fifth pressure pad.

According to another aspect, a truss pad may comprise a base body, wherein the base body may comprise a first surface and a second surface opposite the first surface, wherein the first surface of the base body may comprise pressure pads, characterized in that the first surface of the base body may comprise five pressure pads, and wherein the first pressure pad is located in the center of a rectangle that is formed by the second pressure pad, the third pressure pad, the fourth pressure pad, and the fifth pressure pad. In some configurations, the base body may comprise the basic shape of a rectangle, the rectangle having rounded corners, and wherein the four rounded corners of the base body may be formed by the second pressure pad, the third pressure pad, the fourth pressure pad, and the fifth pressure pad.

In some configurations, the base body may have a basic shape of a rectangle, wherein the rectangle has four rounded corners, and wherein the four rounded corners of the base body are formed by the second pressure pad, the third pressure pad, the fourth pressure pad, and the fifth pressure pad.

In some configurations, the base body of the truss pad may comprise a recess between the second pressure pad and the third pressure pad, between the third pressure pad and the fourth pressure pad, between the fourth pressure pad and the fifth pressure pad, and between the fifth pressure pad and the second pressure pad.

According to another aspect, the truss pad may comprise a base body having indentations between the pressure pads.

According to yet another aspect, the truss pad may comprise a rectangle having two long sides and two short sides, and wherein the long sides are about at least 1.2 times to at most 2.5 times as long as the short sides.

In some aspects, the five pressure pads of the truss pad may comprise, in longitudinal section, a round or ellipsoidal interface and the five pads may protrude in a bubble-like manner from the base body.

According to another aspect, the truss pad may be made of a viscoelastic material. According to another aspect, disclosed herein is an epicondylitis brace, epicondylitis bandage, or epicondylitis orthosis comprising a truss pad according to claim 1 and a truss pad carrier. The epicondylitis brace, epicondylitis bandage, or epicondylitis orthosis may comprise a truss pad reversibly connected to the truss pad carrier via a hook-and-loop connection. The epicondylitis brace, epicondylitis bandage, or epicondylitis orthosis may comprise a truss pad enclosed in a soft casing and the casing may be reversibly connected to the truss pad carrier via a hook-and-loop connection.

BRIEF DESCRIPTION OF THE SEVERAL VIEWS OF THE DRAWINGS

The present invention is explained with reference to the exemplary figures below, without the object of the figures being understood as limiting.

Shown are.

DETAILED DESCRIPTION

Figure 1:
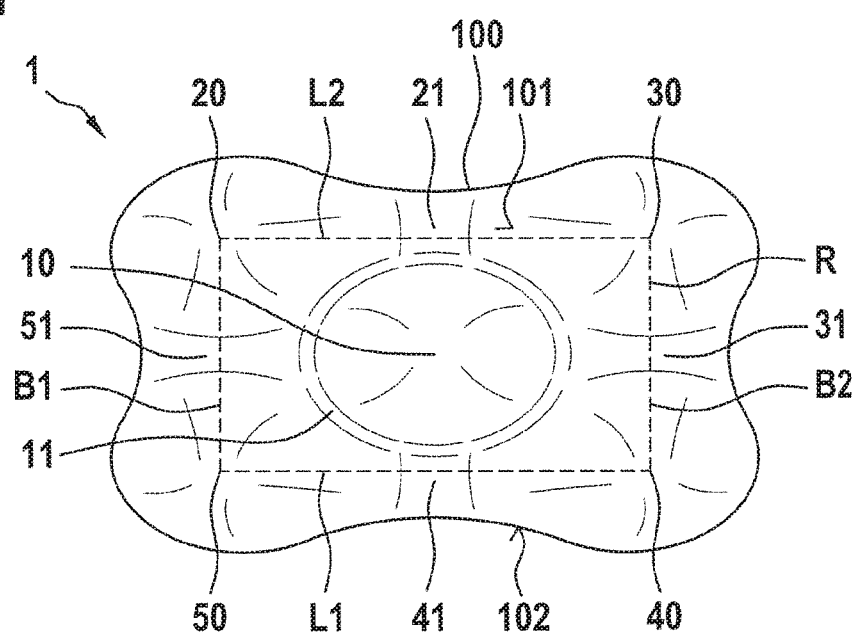
FIG. 1 the top view of a truss pad according to the invention.

The truss pad according to the invention, also called epicondylitis truss pad, is characterized by positioning five pressure pads on the surface of the truss pad abutting against the skin. The specific positioning of the pressure pads advantageously allows the use of the truss pad both on the right arm and on the left arm without the positioning of the truss pad on the epicondylitis brace, epicondylitis bandage, or epicondylitis orthosis having to be changed fundamentally. The positioning of the pressure pads moreover allows treatment of both tennis elbow and golf elbow. The present invention therefore also relates to the use of the truss pad according to the invention to treat tennis elbow and/or golf elbow.

The invention is based on the task of creating an epicondylitis truss pad with which adjustable pressure introduction onto the epicondyle can be achieved in a therapeutically particularly favorable manner independently of whether the truss pad is placed on the right or left arm and wherein the truss pad does not have to be elaborately remounted when changing to the other arm. At the same time, the invention is based on the task of providing a truss pad with which both tennis elbows and golf elbows can be respectively treated at the therapeutically correct point, in particular be treated simultaneously, namely optionally on the right or left arm.

The invention solves the underlying technical problem by means of a truss pad having a base body, wherein the base body comprises a first surface and a second surface opposite the first surface, wherein the first surface of the base body comprises five pressure pads, and wherein the first pressure pad is positioned at the center of a rectangle that is formed by the second pressure pad, the third pressure pad, the fourth pressure pad, and the fifth pressure pad. According to the invention, the five pressure pads are thus positioned symmetrically on the base body.

The pressure pads are positioned such that they push on and massage specific nerve ends during use of the truss pad so that the pain after overexertion, for example by playing tennis or golf, is alleviated. Trigger points are locally limited muscle hardenings in the skeletal muscles that are locally sensitive to pressure and from which transferred pain can originate. By means of the arrangement according to the invention of the five pressure pads, trigger points of muscles that start laterally (epicondylus humeri radii) or medially (epicondylus humeri ulnae) at bone protuberances or pass by, such as in the case of the musculus brachioradialis, are reached. In particular, not only the trigger points located laterally on the elbow, e.g., on the musculus extensor carpi radialis longus and musculus extensor carpi radialis brevis and on the musculus brachioradialis, can be reached, which play a role in the case of a tennis elbow, but also medial trigger points, e.g., those of the musculus pronator teres, musculus palmaris longus, musculus flexor carpi ulnaris, and musculus flexor carpi radialis, which play a role in the case of a golf elbow. While the two lateral trigger points can thus be used to treat the pain of a tennis elbow, the medial trigger points are suitable for treatment of golf elbow. By means of the truss pad according to the invention, both tennis elbow and golf elbow can therefore be treated, even simultaneously, without the truss pad having to have its position changed, e.g. be turned. In addition, the positioning according to the invention of the five pressure pads results in the truss pad being able to be used on the right and on the left arm without repositioning, e.g., turning, the truss pad on the holding means, e.g., an epicondylitis brace or epicondylitis bandage. Thus, advantageously provided is a truss pad that can already be connected to the holding means at the time of delivery such that it is positioned appropriately for any indication and correctly for anybody regardless of whether the truss pad is provided for the treatment of a tennis elbow and/or of a golf elbow and regardless of whether the truss pad is provided for the treatment of a left arm or a right arm.

In comparison to the truss pad from DE 197 16 705 C1, which comprises three elevations, the truss pad according to the invention has five pressure pads and the pressure pads are positioned and spaced apart differently.

In one embodiment, the truss pad comprises exactly five pressure pads. In one configuration, the truss pad consists of five pressure pads.

The first surface of the base body comprises the pressure pads and is thus the surface that faces the arm when the truss pad is placed on the arm. The opposite second surface thus faces away from the arm and can, for example, be connected to a truss pad carrier, i.e., a carrier element that carries the truss pad, an epicondylitis brace, an epicondylitis bandage, or an epicondylitis orthosis, e.g., reversibly, in particular via a hook-and-loop fastener. The second surface preferably comprises a hook surface section and a loop surface section. The truss pad is preferably surrounded by a soft, textile casing. The casing preferably comprises a hook surface section and a loop surface section.

In one configuration, the second pressure pad, the third pressure pad, the fourth pressure pad, and the fifth pressure pad are respectively located at a corner of the first surface of the base body.

In one configuration, the base body is formed from the five pressure pads, which are thus in this case connected directly to one another, wherein the connection points form indentations between the pressure pads.

In one configuration, the base body has approximately the basic shape of a rectangle, in particular of the rectangle that is formed by the four outer pressure pads, wherein the rectangle has rounded corners and wherein the four rounded corners of the base body are preferably formed by the second pressure pad, the third pressure pad, the fourth pressure pad, and the fifth pressure pad.

The base body itself however does not have to be rectangular but can have a different shape. For example, recesses between the pressure pads forming the corner points can be provided in the base body so that a bone-like basic shape of the base body is formed.

In one configuration, the base body respectively comprises a recess between the second pressure pad and the third pressure pad, between the third pressure pad and the fourth pressure pad, between the fourth pressure pad and the fifth pressure pad, and between the fifth pressure pad and the second pressure pad.

In one configuration, the base body comprises indentations between the pressure pads.

The indentations constitute the transitions between adjacent pressure pads or the indentations constitute the basic thickness of the truss pad base body from which the pressure pads protrude.

In one configuration, the rectangle has two long sides and two short sides, wherein the long sides are at least 1.2 times to at most 2.5 times as long as the short sides.

The long sides are preferably approximately 1.5 to 2 times as long as the short sides. The long sides, as the outer edges of the base body, are preferably approximately 4 to 8 cm long, particularly preferably approximately 6 cm long, and the short sides, as outer edges of the base body, are approximately 2 to 5 cm long, in particular approximately 4 cm long. The long sides, as connection of the highest points of two pressure pads, are approximately 3 to 5 cm long, particularly preferably approximately 4 cm long, and the short sides, as connection of the highest points of two pressure pads, are approximately 1 to 3 cm long, in particular approximately 2 cm long. The highest points of an outside pressure pad and of the center pressure pad are preferably spaced apart at a distance of approximately 2 cm, in particular at least 1.8 cm and at most 2.3 cm, from each other.

The pressure pads preferably protrude approximately 0.2 cm to approximately 1 cm, in particular approximately 0.5 cm, from the base body. The truss pad preferably has a greatest thickness at the pressure pads of approximately 0.5 cm to approximately 2 cm, in particular of at most approximately 1 cm.

In one configuration, the five pressure pads comprise, in longitudinal section, a round or ellipsoidal interface, wherein the five pressure pads protrude in a bubble-like manner from the base body.

The pressure pads thus preferably protrude from the base body as rounded bulges that can be circular or ellipsoidal.

Advantageously, it is completely sufficient for the exertion of pressure that the pressure pads have a smooth surface. The exertion of pressure by the pressure pads can however be further intensified by providing the pressure pads with a profiled surface, which results in additional friction or massage.

In one configuration, the truss pad is made of a viscoelastic material. Suitable materials are known to the person skilled in the art.

The truss pad according to the invention can be used first and foremost during sports, e.g., when playing tennis or golf.

The truss pad according to the invention can be used preventively in order to avoid discomfort or to alleviate discomfort in the elbow region, e.g., during sports.

The truss pad is preferably used non-medically. A medically indicated use is however also possible.

The present invention also relates to an epicondylitis brace, epicondylitis bandage, or epicondylitis orthosis comprising a truss pad according to the invention and a truss pad carrier.

Suitable epicondylitis braces, epicondylitis bandages, and epicondylitis orthoses, to which a truss pad, and in particular the truss pad according to the invention, can be attached via a truss pad carrier, are sufficiently known to the person skilled in the art, e.g., from DE 197 16 705 C1. For example, in the epicondylitis brace shown in DE 197 16 705 C1, the triangular truss pad used there can be replaced by the truss pad according to the invention.

In such an epicondylitis brace or epicondylitis bandage, the brace element or the bandage element forms the truss pad carrier that holds the truss pad. In this case, the truss pad is preferably positioned on the brace or on the bandage such that the long sides of the truss pad extend almost parallel to the long sides of the brace or of the bandage, which surround the arm. In this case, one configuration can provide that the truss pad is connected reversibly to the truss pad carrier, even if a fundamental repositioning of the truss pad is no longer necessary as a result of the use of the truss pad according to the invention. A reversible attachment is however advantageous in order to allow a minimal readjustment of the truss pad position on the truss pad carrier. The truss pad, in particular the second surface of the truss pad, is thus preferably connected to the truss pad carrier via a holding means, in particular a releasable holding means.

An appropriate attachment of the truss pad can consist of a hook-and-loop fastener that forms the holding means and is attached on the one hand to the truss pad carrier and on the other hand to the truss pad or the casing of the truss pad, wherein the second surface of the truss pad is connected to the truss pad carrier. It is however also possible to form the holding means as latch pins and bores receiving them. In this case, the latch pins can be formed on the truss pad and the associated bores can be formed on the brace but is also possible to form the latch pins on the brace and the receiving bores on the truss pad. In one configuration, the truss pad is however reversibly connected to the truss pad carrier via a hook-and-loop connection.

In one configuration, the truss pad is enclosed in a soft, textile casing and the casing is reversibly connected to the truss pad carrier via a hook-and-loop connection.

Disclosed herein is an epicondylitis brace having a clamp that contains a spring strap and that can be contracted by an infinitely adjustable retaining strap, wherein a truss pad according to the invention is arranged on the one end of the clamp on the inside of the brace, wherein the truss pad is preferably reversibly connected to the inside of the brace.

The epicondylitis brace, epicondylitis bandage, or epicondylitis orthosis is preferably a sports product, which is preferably used non-medically. A medical use is however also possible.

The present invention also relates to the use of a truss pad according to the invention, an epicondylitis brace according to the invention, an epicondylitis bandage according to the invention, and an epicondylitis orthosis according to the invention as a sports product or while doing sports, e.g., when playing tennis or golf.

The present invention also relates to the use of a truss pad according to the invention, an epicondylitis brace according to the invention, an epicondylitis bandage according to the invention, or an epicondylitis orthosis according to the invention for the prevention of discomfort in the elbow region, in particular for the prevention of a tennis elbow and/or golf elbow.

The present invention also relates to the use of a truss pad according to the invention, an epicondylitis brace according to the invention, an epicondylitis bandage according to the invention, or an epicondylitis orthosis according to the invention for the treatment of a tennis elbow and/or a golf elbow. The present invention also relates to a method for treating a tennis elbow and/or a golf elbow in which a truss pad according to the invention is pressed onto the elbow to be treated, e.g., via an epicondylitis brace according to the invention, an epicondylitis bandage according to the invention, or an epicondylitis orthosis according to the invention, so that the five pressure pads push on appropriate trigger points, in particular the trigger points located laterally on the elbow on the musculus brachioradialis and the medial trigger points of the musculus pronator teres, musculus palmaris longus, musculus flexor carpi ulnaris, and/or musculus flexor carpi radialis.

Additional configurations result from the dependent claims.

FIG. 1 shows a top view of a truss pad (1) according to the invention. For this reason, the first surface (101) of the base body (100) of the truss pad (1) can be seen but not the second surface (102). Five pressure pads (10, 20, 30, 40, 50) protrude from the base body (100). In this case, the second pressure pad (20), the third pressure pad (30), the fourth pressure pad (40), and the fifth pressure pad (50) form an imaginary rectangle (R). The first pressure pad (10) is located in the center of the rectangle (R). The imaginary rectangle (R), the corners of which are formed by the highest points of the four outside pressure pads (20, 30, 40, 50), has two long sides (L1, L2) of a length of approximately 4 cm and two short sides (B1, B2) of a length of approximately 2 cm. Indentations (11, 21, 31, 41, 51) are located between the pressure pads (10, 20, 30, 40, 50).

The shown truss pad according to the invention has a shape and size with which the five pressure pads (10, 20, 30, 40, 50) can advantageously push on five trigger points in the elbow region, namely both on trigger points on the lateral bone protuberances in order to treat tennis elbow and on trigger points on the medial bone protuberances in order to treat golf elbow.

The treatment of a tennis elbow and/or golf elbow is thus possible.

Figure 2:
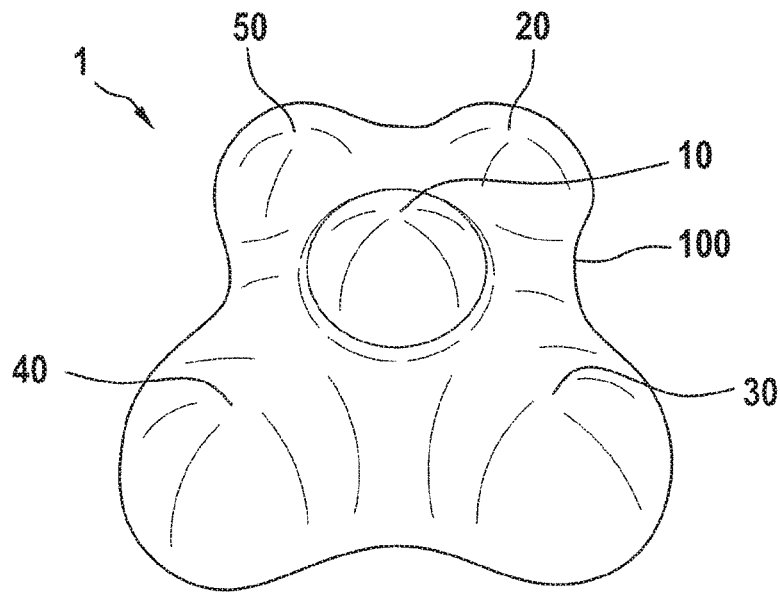
FIG. 2 the oblique view of a truss pad according to the invention from a short side, FIG. 3 the oblique view of a truss pad according to the invention from a long side, FIG. 4 a truss pad according to the invention on a truss pad carrier of an epicondylitis brace or an epicondylitis bandage, FIG. 5 a truss pad according to the invention on an embodiment of an epicondylitis brace.

FIG. 2 shows the truss pad (1) according to the invention having the base body (100) and the pressure pads (10, 20, 30, 40, 50) from FIG. 1 designed as elevations in oblique view from the short side.

Figure 3:
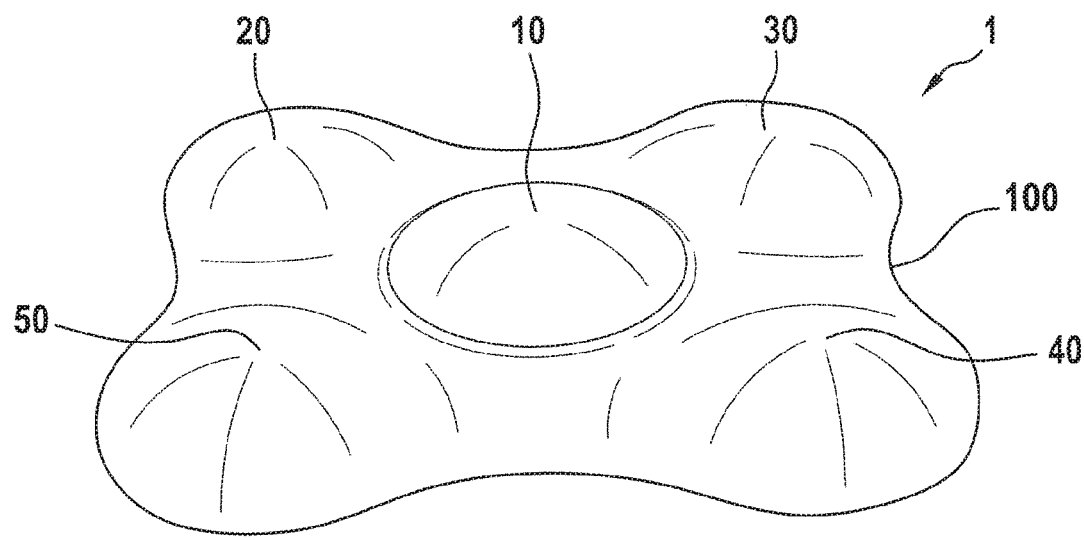

FIG. 3 shows the truss pad (1) according to the invention having the base body (100) and the pressure pads (10, 20, 30, 40, 50) from FIG. 1 designed as elevations in oblique view from the long side.

Figure 4:
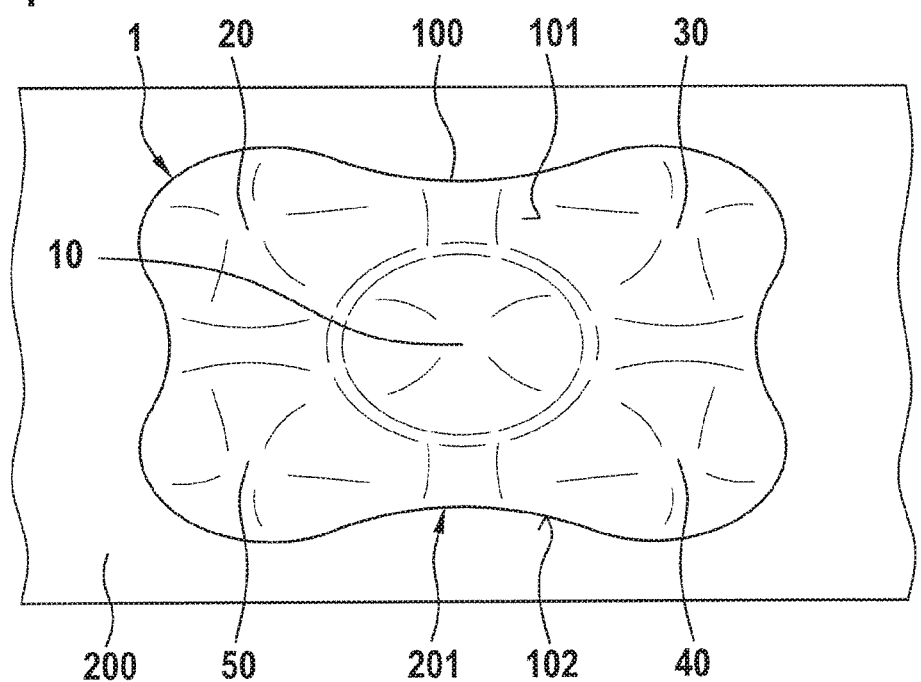

FIG. 4 shows a truss pad (1) according to the invention having the base body (100) and the five pressure pads (10, 20, 30, 40, 50) of the first surface (101) on a truss pad carrier (200). With the non-visible second surface (102), which forms the rear side of the truss pad, the truss pad (1) is reversibly connected to the truss pad carrier (200) via a non-visible hook-and-loop connection (201) consisting of a hook layer and a loop layer. The truss pad carrier (200) can be a component of an epicondylitis brace, an epicondylitis bandage, or an epicondylitis orthosis. As the person skilled in the art knows, the epicondylitis brace, epicondylitis bandage, or epicondylitis orthosis is placed around the forearm in the region of the elbow so that the truss pad (1) pushes with the pressure pads (10, 20, 30, 40, 50) on the trigger points there, wherein the truss pad (1) is pressed onto the arm by the truss pad carrier (200).

Figure 5:
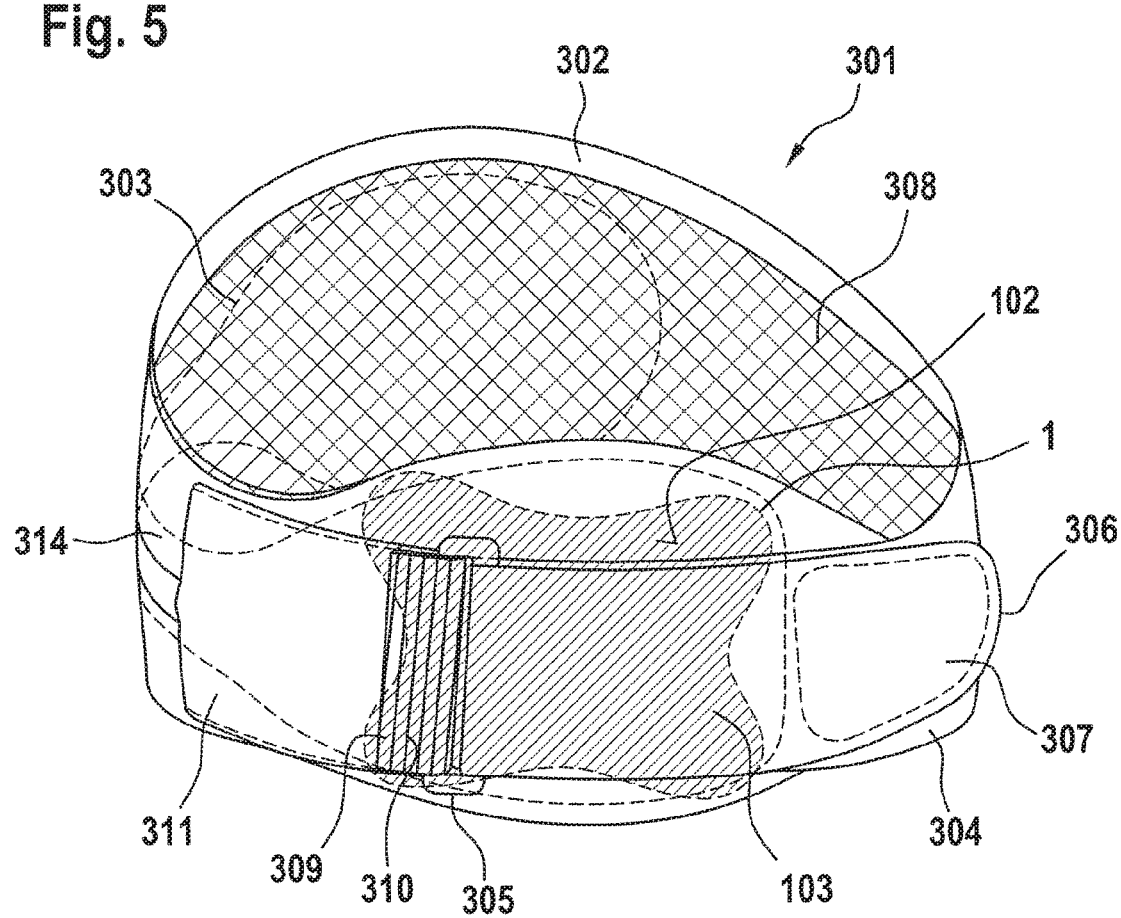

FIG. 5 shows an epicondylitis brace (301) that is based on the brace design shown in DE 197 16 705 C1 and that consists of a clamp (302) having a spring strap (303) contained therein. The spring strap (303) is glued into the clamp (302). The clamp (302) transitions into the retaining strap (304), which is narrower in comparison to the clamp (302) and which is looped through the deflection element (305) in the shape of an elongate eyelet shown closed in the illustration and the end (306) of which is placed over the beginning of the retaining strap (304), where it is firmly held on the retaining strap (304) by means of the hook-and-loop fastener (307). On its inside, the clamp (302) is provided with a textile overlay (308) (cross-hatched), which makes wearing the epicondylitis brace easier. The deflection element (305) is attached to the clamp (302) via the elastic strap (309), which is provided with a plurality of transverse seams (310). On its side facing away from the deflection element, the elastic strap (309) extends in the pocket (311), which is applied onto the clamp (302) and in which the elastic strap (309) is attached to the clamp (302). The clamp (302) envelops the spring strap (303) contained therein with a cover on textile material, which cover transitions into the retaining strap (304) and, with its hook elements, forms the associated loop part for the hook-and-loop fastener (307). The spring strap (303) has a weakening (314), as a result of which the spring strap (303) is significantly narrowed in comparison to its end regions. Due to this weakening (314) of the spring strap (303), the weakening (314) gives the spring strap (303) a certain hinge effect in the region of the weakening (314) so that the part of the clamp (302) carrying the truss pad (1) bends inwardly relative to the other rounding of the clamp (302) when the retaining strap (304) is pulled tight and thus is able to exert a particular pressure on the part of the forearm located there.

Further shown is a truss pad (1) according to the invention, which is drawn with dashes and which is arranged on the inside of the clamp (302) in the position of the epicondylitis brace (301) shown closed and is therefore shown as non-visible in FIG. 5. The truss pad is enclosed in a textile casing (103). The textile casing is attached to the clamp (302) via a hook-and-loop fastener (201) so that the second surface (102) of the truss pad (1) abuts against the clamp (302).

The invention claimed is:

1. An epicondylitis brace, epicondylitis bandage, or epicondylitis orthosis comprising a truss pad and a truss pad carrier, wherein the truss pad comprises a base body, wherein the base body comprises a first surface, the first surface being a continuous surface, and a second surface opposite the first surface, wherein the first surface of the base body comprises pressure pads, characterized in that the first surface of the base body comprises exactly five pressure pads,
wherein the first pressure pad is located in a center of a rectangle that is formed by the second pressure pad, the third pressure pad, the fourth pressure pad, and the fifth pressure pad.

2. The epicondylitis brace, epicondylitis bandage, or epicondylitis orthosis comprising the truss pad according to claim 1, wherein the base body has a basic shape of the rectangle, wherein the rectangle has four rounded corners, and wherein the four rounded corners of the base body are formed by the second pressure pad, the third pressure pad, the fourth pressure pad, and the fifth pressure pad.

3. The epicondylitis brace, epicondylitis bandage, or epicondylitis orthosis comprising the truss pad according to claim 2, wherein the base body respectively comprises a recess between the second pressure pad and the third pressure pad, between the third pressure pad and the fourth pressure pad, between the fourth pressure pad and the fifth pressure pad, and between the fifth pressure pad and the second pressure pad.

4. The epicondylitis brace, epicondylitis bandage, or epicondylitis orthosis comprising the truss pad according to claim 1, wherein the base body respectively comprises a recess between the second pressure pad and the third pressure pad, between the third pressure pad and the fourth pressure pad, between the fourth pressure pad and the fifth pressure pad, and between the fifth pressure pad and the second pressure pad.

5. The epicondylitis brace, epicondylitis bandage, or epicondylitis orthosis comprising the truss pad according to claim 1, wherein the rectangle has two long sides and two short sides and wherein the long sides are at least 1.2 times to at most 2.5 times as long as the short sides.

6. The epicondylitis brace, epicondylitis bandage, or epicondylitis orthosis comprising the truss pad according to claim 1, wherein the truss pad is made of a viscoelastic material.

7. The epicondylitis brace, epicondylitis bandage, or epicondylitis orthosis according to claim 1, wherein the truss pad is reversibly connected to the truss pad carrier via a hook-and-loop connection.

8. The epicondylitis brace, epicondylitis bandage, or epicondylitis orthosis according to claim 7, wherein the truss pad is enclosed in a soft casing and the casing is reversibly connected to the truss pad carrier via a hook-and-loop connection.

9. The epicondylitis brace, epicondylitis bandage, or epicondylitis orthosis according to claim 1, wherein the truss pad is enclosed in a soft casing and the casing is reversibly connected to the truss pad carrier via a hook-and-loop connection.

10. An epicondylitis brace, epicondylitis bandage, or epicondylitis orthosis comprising a truss pad and a truss pad carrier, wherein the truss pad comprises a base body, wherein the base body comprises a first continuous surface and a second surface opposite the first surface, wherein the first surface of the base body comprises pressure pads, characterized in that the first surface of the base body comprises five pressure pads,
wherein the first pressure pad is located in a center of a rectangle that is formed by the second pressure pad, the third pressure pad, the fourth pressure pad, and the fifth pressure pad;
wherein the base body comprises the basic shape of the rectangle, wherein the rectangle has rounded corners, and wherein the four rounded corners of the base body are formed by the second pressure pad, the third pressure pad, the fourth pressure pad, and the fifth pressure pad.

11. The epicondylitis brace, epicondylitis bandage, or epicondylitis orthosis comprising the truss pad according to claim 10, wherein the base body comprises indentations between the pressure pads.

12. The epicondylitis brace, epicondylitis bandage, or epicondylitis orthosis comprising the truss pad according to claim 10, wherein the five pressure pads comprise, in longitudinal section, a round or ellipsoidal interface and wherein the five pads protrude in a bubble-like manner from the base body.

13. The epicondylitis brace, epicondylitis bandage, or epicondylitis orthosis comprising the truss pad according to claim 10, wherein the base body respectively comprises a recess between the second pressure pad and the third pressure pad, between the third pressure pad and the fourth pressure pad, between the fourth pressure pad and the fifth pressure pad, and between the fifth pressure pad and the second pressure pad.

14. A system for treating or preventing epicondylitis comprising:
at least one of an epicondylitis brace, epicondylitis bandage, and epicondylitis orthosis comprising:
a truss pad and a truss pad carrier, wherein the truss pad comprises a base body, the base body having a first, continuous surface and a second surface opposite the first surface, wherein the first surface of the base body comprises pressure pads, characterized in that the first surface of the base body comprises five pressure pads, the five pressure pads configured to put pressure on trigger points on one or more lateral bone protuberances and one or more medial bone protuberances.

15. The system of claim 14, wherein the five pressure pads comprise a first pressure pad, a second pressure pad, a third pressure pad, a fourth pressure pad, and a fifth pressure pad and wherein the first pressure pad is located in a center of a rectangle that is formed by the second pressure pad, the third pressure pad, the fourth pressure pad, and the fifth pressure pad.

16. The system of claim 14, wherein the five pressure pads are configured to put pressure on trigger points on at least one of a musculus extensor carpi radialis longus, a musculus extensor carpi radialis brevis, and a musculus brachioradialis, and wherein the five pressure pads are also configured to put pressure on trigger points on at least one of a musculus pronator teres, a musculus palmaris longus, a musculus flexor carpi ulnaris, and a musculus flexor carpi radialis.

* * * * *